(12) United States Patent
Timmermans et al.

(10) Patent No.: US 7,585,110 B2
(45) Date of Patent: Sep. 8, 2009

(54) X-RAY EXAMINATION APPARATUS

(75) Inventors: Roger Anton Marie Timmermans, Eindhoven (NL); Raymond Wilhelmus Louis Lafarre, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/065,626

(22) PCT Filed: Sep. 8, 2006

(86) PCT No.: PCT/IB2006/053168

§ 371 (c)(1),
(2), (4) Date: Mar. 4, 2008

(87) PCT Pub. No.: WO2007/029202

PCT Pub. Date: Mar. 15, 2007

(65) Prior Publication Data

US 2008/0198973 A1    Aug. 21, 2008

(30) Foreign Application Priority Data

Sep. 9, 2005    (EP) .................................. 05108297

(51) Int. Cl.
   *H05G 1/02* (2006.01)
(52) U.S. Cl. ...................................... 378/197; 378/196
(58) Field of Classification Search .......... 378/196–198
   See application file for complete search history.

(56) References Cited

U.S. PATENT DOCUMENTS

| | | | | | |
|---|---|---|---|---|---|
| 4,541,293 | A | * | 9/1985 | Caugant et al. | 74/89.18 |
| 5,050,204 | A | * | 9/1991 | Siczek et al. | 378/197 |
| 5,450,466 | A | * | 9/1995 | Kadowaki et al. | 378/194 |
| 5,515,416 | A | * | 5/1996 | Siczek et al. | 378/197 |
| 6,113,264 | A | * | 9/2000 | Watanabe | 378/197 |
| 6,203,196 | B1 | | 3/2001 | Meyer et al. | |
| 6,325,537 | B1 | * | 12/2001 | Watanabe | 378/197 |
| 6,619,840 | B2 | * | 9/2003 | Rasche et al. | 378/197 |
| 6,742,929 | B2 | * | 6/2004 | Horbaschek | 378/197 |
| 2002/0118793 | A1 | | 8/2002 | Horbaschek | |
| 2003/0072416 | A1 | | 4/2003 | Rasche et al. | |
| 2006/0023830 | A1 | * | 2/2006 | Schomberg | 378/4 |

FOREIGN PATENT DOCUMENTS

| | | |
|---|---|---|
| DE | 19855213 C2 | 11/1998 |
| DE | 19855213 A1 | 6/2000 |

(Continued)

*Primary Examiner*—Edward J Glick
*Assistant Examiner*—Thomas R Artman

(57) ABSTRACT

An X-ray examination apparatus (10) comprises radiation modules in the form of an X-ray source (20) and an X-ray detector (18), a main curved arm (12) having opposite end sections (S1, S2) and a first auxiliary arm (14) provided at one end section (S1) of the main arm. The first auxiliary arm carries one radiation module (18) and another radiation module (20) is coupled to the other end section of the main arm. The first auxiliary arm has a shape that complements the curvature of the main curved arm at least at the first end section and is movable with respect to this end section at least in a direction away from it. In this way a wide range of inspection angles as well as a good patient coverage is achieved without limiting the rotational freedom of the apparatus.

14 Claims, 3 Drawing Sheets

FOREIGN PATENT DOCUMENTS

| | | |
|---|---|---|
| JP | 2002119500 | 4/2002 |
| JP | 2002119500 A | 4/2002 |
| WO | WO03/054577 A1 | 7/2003 |
| WO | WO03054577 A1 | 7/2003 |
| WO | WO2005013828 A1 | 2/2005 |
| WO | WO2005058163 | 6/2005 |
| WO | WO2005058163 A2 | 6/2005 |

* cited by examiner

X-RAY EXAMINATION APPARATUS

TECHNICAL FIELD

The present invention is generally related to the field of medical inspection devices. The present invention is more particularly directed towards an X-ray examination apparatus comprising a main curved arm.

BACKGROUND OF THE INVENTION

In the field of X-ray examining apparatuses for inspecting the bodies of patients, there are continuous efforts being made for designing the examining apparatuses to allow the coverage of as much of the body as possible and to provide as wide angles of inspection of the body as possible. This does also have to be combined with an ergonomically well functioning apparatus for the staff handling it. This means that the medical staff should be able to easily access the patient in order to for instance perform operations while at the same time not having to change the position of the patient when inspections of the patient are to be made from various angles. This is quite a challenge.

In doing this there have been a number of solutions proposed for examining apparatuses using radiation sources. One such solution is the so called C-arc solution, where an X-ray source is provided at one end of a C-shaped arm or arc and an X-ray detector is provided at the other end of the C-shaped arm facing the X-ray source. The C-shaped arm can then be turned round an isocentre using a guiding system. This C-shaped system allows large rotation angles but is however normally limited regarding patient coverage, i.e. it is normally not possible to inspect the whole body of the patient without moving the patient.

Another system is the so called G-based system, where a G-shaped arm or arc is used instead. This arc allows better patient coverage but is however more limited regarding supported inspection angles.

U.S. Pat. No. 6,203,196 describes a C-shaped arc which has received straight add-on elements. On these add-on elements there are provided bars that can move telescopically out from the ends of the C-shaped arc. This has the advantage of allowing a better patient coverage. However these add-on elements limit the rotational freedom of the C-shaped arc.

It would therefore be of interest to provide better patient coverage in an X-ray examining apparatus while at the same time not limiting the rotational freedom of the apparatus.

SUMMARY OF THE INVENTION

One object of the present invention is therefore to provide an improved X-ray examining apparatus, and particularly one which provides good patient coverage at the same time as it does not limit the rotational freedom of the apparatus.

According to the present invention, this object is achieved by an X-ray examination apparatus comprising:

radiation modules in the form of an X-ray source and an X-ray detector,
a main curved arm having opposite end sections,
a first auxiliary arm provided at one end section of the main arm,
the first auxiliary arm carrying one radiation module,
another radiation module being coupled to the other end section of the main arm,
the first auxiliary arm having a shape that complements the curvature of said main curved arm at least at said first end section and being movable with respect to this end section of the main arm at least in a direction away from it.

With the present invention it is possible to use an X-ray examining apparatus that can make larger projection angles. At the same time patient coverage can be increased in a simple manner. The rotational freedom of the apparatus is not limited since the structure provides for the auxiliary arm to be moved within the system volume, where the system volume is defined by the shape of the main curved arm, as well as its distance to and full rotation round at least one rotational axis defined through an isocentre of the system. There is furthermore no additional space occupied by the apparatus when such turning is performed. The apparatus is furthermore very general in nature and can be used for a multitude of applications. The apparatus further includes a limited number of parts, which makes it easy to implement and provides a compact design.

According to claim 2 the first auxiliary arm is being movable with respect to its end section of the main arm in a direction inwards along the first end section. This has the advantage of allowing larger projection angles.

According to claim 3, a second auxiliary arm is provided at the second end section of the main arm carrying one radiation module. This feature has the advantage of allowing even larger projection angles and providing a wider patient coverage.

According to claim 4, the second auxiliary arm is being movable with respect to its end section of the main arm in a direction inwards along the second end section. This has the advantage of allowing even larger projection angles.

According to claim 5, the combined lengths of the first and second auxiliary arms are equal to or less than the length of the main arm. This feature allows a great flexibility in the design of the auxiliary arms while at the same time limiting the movement of the auxiliary arms to within the system volume.

According to claim 6, each radiation module is connected to a corresponding arm using a mechanical coupler, where each coupler essentially allows the turning of a radiation module round an axis of rotation provided through the corresponding mechanical coupler that is transverse to the movement of the auxiliary arm. This feature has the advantage of allowing the radiation modules to be aligned with each other when a larger coverage area is provided.

According to claim 7, one mechanical coupler provided for one radiation module is connected to a bar stretching inwards in a direction essentially towards the other radiation module allowing movement of this radiation module along the bar. This feature has the advantage of allowing the provision of the same distance between the radiation modules for all positions of the apparatus.

Claims 8, 9 and 10 are directed towards providing a holder having a Z-drive structure for rotating the main arm. This structure has the advantage of allowing the main curved arm to be rotated with larger angles than conventional drive structures.

According to claim 11 one radiation module is connected to the main arm. This has the advantage of limiting the number of movable arms when a Z-drive structure is used, while still ensuring a wider patient coverage According to claim 12 there is a motion control unit arranged to control the movements of all movable elements of the apparatus to make the radiation modules always face each other.

According to one advantageous variation of the present invention, the main curved arm has the shape of a part of a circle. This has the advantage of allowing placing of the radiation modules with the same distance between each other when providing a wide range of inspection angles.

According to another advantageous variation of the present invention, the main curved arm has the shape of approximately half a circle. This feature has the advantage of providing wide angles combined with a limited size of the main arm.

The basic idea of the invention is to provide an X-ray examining apparatus having radiation modules in the form of an X-ray source and an X-ray detector, a main curved arm having opposite end sections, a first auxiliary arm provided at one end section of the main arm, where the first auxiliary arm carries one radiation module and another radiation module is coupled to the other end section of the main arm. The first auxiliary arm has a shape that complements the curvature of the main curved arm at least at the first end section and can be moved in relation to this end section at least in a direction away from it. In this way a wide range of inspection angles as well as a good patient coverage is achieved without limiting the rotational freedom of the apparatus.

The above mentioned and other aspects of the invention will be apparent from and elucidated with reference to the embodiments described hereinafter.

BRIEF DESCRIPTION OF THE DRAWINGS

The present invention will be further described in relation to the accompanying drawings, in which.

DETAILED DESCRIPTION OF THE INVENTION

Figure 1:
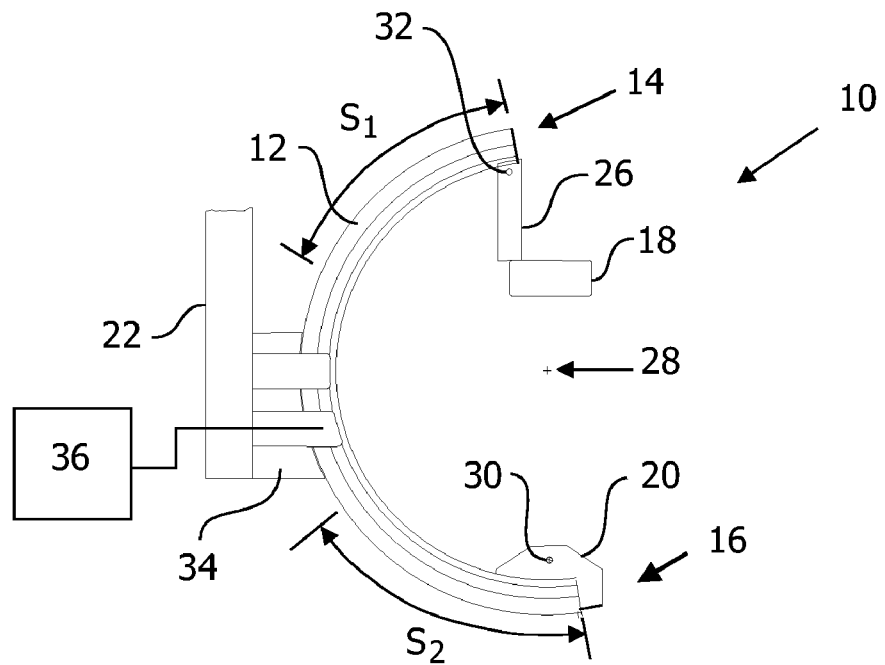
FIG. 1 shows a side view of an X-ray examination apparatus according to a first embodiment of the present invention in a nominal position and having a main arm and two auxiliary arms.

The present invention is generally directed towards an X-ray examination apparatus using X-ray radiation for inspecting the body of a patient. In the following an apparatus will be described having a C-shaped main arm or arc. It should however be realized that the present invention can be used with other configurations of the main arm, like for instance a G-shaped arm as long as at least the main arm moves around an isocentre.

FIG. 1-4 show side views of an apparatus 10 according to a first embodiment of the present invention in different positions. In these drawings there is provided a main curved arm 12, which is here shaped as half a circle or a C. The main arm 12 is furthermore fastened to a holder 22, which includes a curved first guiding system 34 that can turn the main arm 12 round an isocentre 28 defined by the curvature of the first guiding system 34. The main arm is in this way rotated round a first rotational axis provided by the first guiding system. This first rotational axis is provided through said isocentre perpendicular to the plane of the paper in FIG. 1. The first guiding system 34 can be provided as a track in which the main arm may run, which track thus has a certain curvature. The holder 22 may furthermore rotate the first guiding system around a second rotational axis stretching from the holder 22 to the isocentre 28, which second axis is thus perpendicular to the first rotational axis. All rotations of the main arm around the isocentre 28 furthermore define a system volume, which system volume is thus decided by the outer shape of the main arm 12, its distance from the isocentre 28 a full rotation of it round the first rotational axis as well as round the second rotational axis, if it is provided. The system volume is thus here essentially spherical if the second rotational axis intersects the first rotational axis in the isocentre. The main arm 12 has a first end section $S_1$ where a first auxiliary arm 14 is provided and a second end section $S_2$, where a second auxiliary arm 16 is provided. The auxiliary arms 14 and 16 are shorter than the main arm 12 and each has a shape that is complimentary to the shape of the main arm 12, which means that they can run along the main arm. They can also run out from the end sections. However, the only part of the main arm that they run along are the end sections, which means that it is sufficient that they are complimentary in shape to these curved end sections. The end sections of the main arm 12 are each hollow and here shaped as a U bar with the ends of the U turned inwards in order to define a second guiding system in the form of a track 38. In this track 38 an auxiliary arm is arranged to run. This configuration is shown in FIG. 5, being exemplified for the second auxiliary arm 16. It should be noted that this is just one way of designing the arms for allowing the auxiliary arms to run along the main arm and that there are countless other ways in which the guiding system could be provided. It is for instance also possible that the auxiliary arm could be provided with a ridge running in a track of the main arm or that the main arm runs in a track provided in an auxiliary arm.

As is mentioned above the auxiliary arms 14 and 16 have a shape that is complementary to the shape of the main arm 12, at least in the end sections $S_1$ and $S_2$ where they are to run. In this way the auxiliary arms 14 and 16 can turn around the isocentre 28. The first and second auxiliary arms are here both shaped such that they are always confined to the system volume. In this way it is ensured that the auxiliary arms do not interfere with the holder or any other equipment used for operating the apparatus or the floor of a room where the apparatus is provided.

The first auxiliary arm 14 is at its furthest end from the centre of the main arm 14 provided with a bar 26 that runs essentially in a direction towards the second auxiliary arm 16. This bar 24 is fastened to the first auxiliary arm via a pivotable mechanical coupler, which is here a first tap 32 providing a first pivot point allowing the bar 26 to turn round this first pivot point. This first tap 32 provides an axis of rotation that is parallel with the previously mentioned first rotational axis and that is thus transverse to the movement of the auxiliary arm. On the bar 26 there is provided a radiation module 18 in the form of an X-ray detector. The X-ray detector 18 can run upwards and downwards along a track provided on the bar. This track makes up a third guiding system, which may be provided in the same way as the second guiding system. The second auxiliary arm 16 has a radiation module 20 in the form of an X-ray source provided at its farthest end from the middle of the main arm 12. The X-ray source 20 is joined to the second auxiliary arm 16 via a pivotable mechanical coupler, which is here a second tap 30 that provides a second pivot point around which the X-ray source 20 may turn. This second tap 30 provides an axis of rotation that also is parallel with the first rotational axis.

WO-03/054577 describes the turning or tilting of an X-ray source for providing different angles of radiation of a spot. In the present invention both an X-ray source and an X-ray detector are turned around pivot points in order to assist in the provision of better patient coverage. How the present invention achieves better patient coverage will shortly be described in more detail.

In order to control the movement of the arms, the bar and the radiation modules, there is provided a motion control unit 36, preferably provided in the form of a processor with associated program memory, which is arranged to emit electrical signals controlling motors (not shown) that control the movement of said arms, bar, radiation units and holder.

Now some ways to use the apparatus according to the first embodiment of the present invention will be described.

In FIG. 1 there is shown a nominal position of the apparatus, which is the normal starting point. Once a patient is to be examined the patient is inserted in the middle of the main arm i.e. between the two ends where the first and second auxiliary arms are provided. This area is thus an inspection area. The isocentre 28 is provided in the middle of this area.

The first and second auxiliary arms 14 and 16 are here positioned at the outermost parts of the end sections $S_1$ and $S_2$, but still within the main arm 12. The X-ray source 20 and X-ray detector 18 are furthermore positioned so that radiation emitted from the X-ray source 20 passes through the isocentre 28 to the X-ray detector 18. The first guiding system 34 furthermore holds the main arm in the middle in between the two end sections. Once a patient is inserted into the inspection area, examination can take place.

Figure 2:
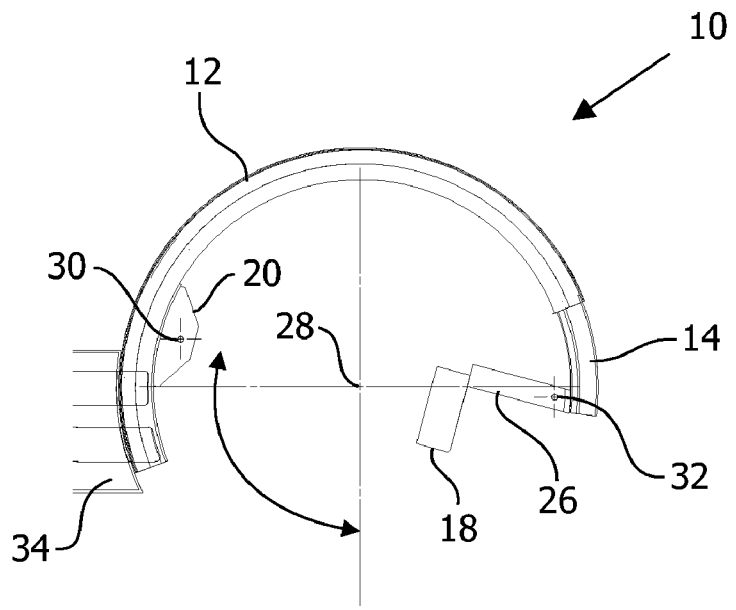
FIG. 2 shows a side view of the X-ray examination apparatus according to the first embodiment of the present invention in a position where the main arm and the auxiliary arms have been turned clockwise around an isocentre.

FIG. 2 shows how the main arm 12 has been turned as far as possible in a clockwise direction. Thus here the first guiding system 34 holds the main arm at its outermost end of the second end section. Also the auxiliary arms 14 and 16 have been moved clockwise as far as possible. Thus the first auxiliary arm 14 has been moved out of the first end section, while the second auxiliary arm has been moved inwards into the second end section with the same amount of movement. At the same time the X-ray source 20 and X-ray detector 18 are facing each other via the isocentre 28. In this way a larger inspection angle is obtained than what could otherwise be obtained if only the main arm 12 was turned. Since movement is made round the isocentre 28 the X-ray source always emits radiation through the isocentre.

Figure 3:
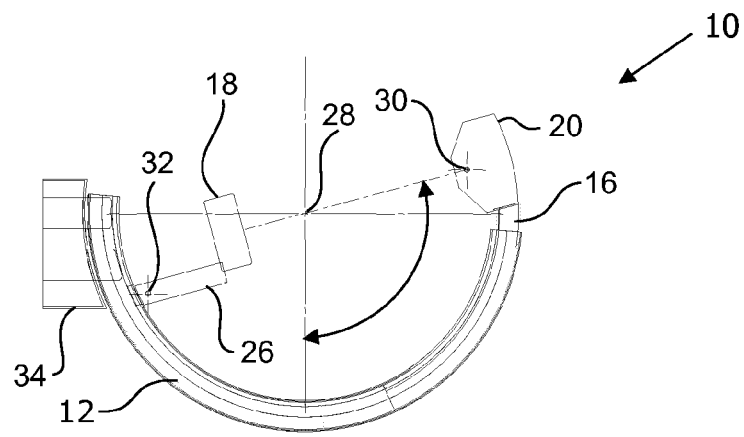
FIG. 3 shows a side view of the X-ray examination apparatus according to the first embodiment of the present invention in a position where the main arm and the auxiliary arms have been turned counterclockwise around the isocentre.

FIG. 3 shows how the opposite type of rotation has been provided. Here the main arm 12 has been moved as far as possible in a counterclockwise direction. Thus here the first guiding system 34 holds the main arm at its outermost end of the first end section. Also the auxiliary arms 14 and 16 have been moved clockwise as far as possible. Thus the second auxiliary arm 16 has been moved out of the end section, while the first auxiliary arm 14 has been moved inwards into the first end section with the same amount of movement. In this way a larger inspection angle is obtained than what could otherwise be obtained if only the main arm was rotated.

Figure 4:
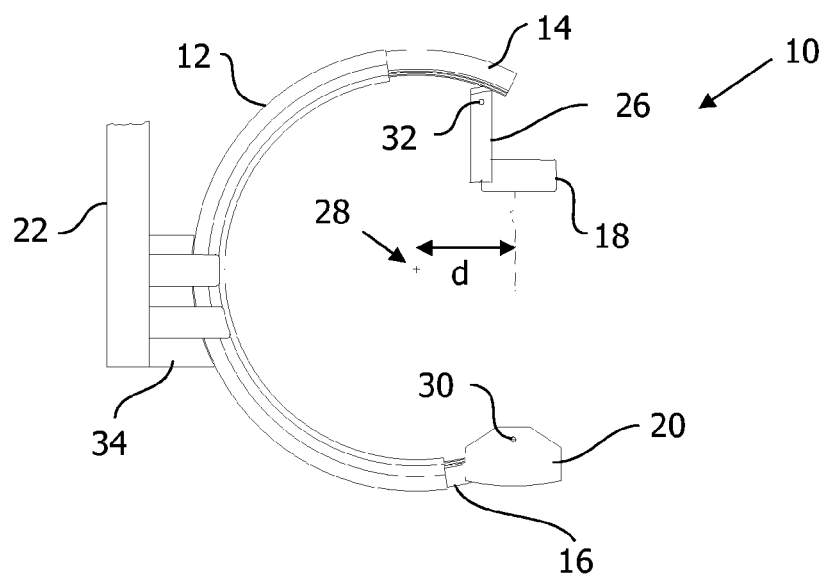
FIG. 4 shows a side view of the X-ray examination apparatus according to the first embodiment of the present invention in a position where the main arm is in the nominal position, while the first auxiliary arm has been turned clockwise and the second auxiliary arm has been turned counterclockwise for movement out of the main arm, FIG. 5 schematically shows a guiding system for the auxiliary arms in the main arm, and FIG. 6 schematically shows a side view of a holder, main arm and first auxiliary arm according to a second embodiment of the present invention.
Figure 5:
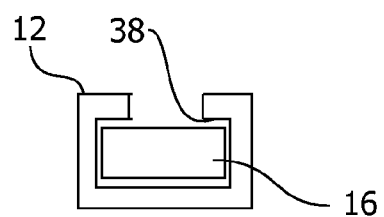

In order to obtain a larger patient coverage the position in FIG. 4 is provided. Here the main arm 12 is held in its nominal position, while the first auxiliary arm 14 has been moved as far as possible in a clockwise direction. At the same time the second auxiliary arm 16 has been moved as far as possible in a counterclockwise direction. Thus here both the auxiliary arms 14 and 16 are moved out from the main arm 12. In this way the X-ray source 20 and the X-ray detector 18 have been displaced a distance d from the isocentre 28 for allowing a larger patient coverage. In order to provide a correct alignment between the X-ray source 20 and the X-ray detector 18, the bar 26 has been turned counterclockwise round the first tap 32 and the X-ray source 20 clockwise round the second tap 30, in order for them to face each other. Finally the X-ray detector 18 can be moved upwards along the bar 26 in order to keep the same distance between the X-ray detector and X-ray source as in the other positions of the apparatus. This is of advantage in that the same energy levels will be measured by the apparatus as in the other positions. This simplifies the analysis of measurement results. This position of the apparatus thus provides a good patient coverage allowing a larger part of the body of a patient to be examined without having to move the patient.

The present invention has a number of advantages. It is possible to make large projection angles and patient coverage can be increased in a simple manner. Since the auxiliary arms are always kept within the system volume, the rotational freedom of the apparatus is not limited. The system is furthermore very general in nature and can be used for a multitude of applications. The apparatus is furthermore provided in a compact form with a limited number of parts. Through the invention it is possible to use a main arm shaped as a C, which allows wider inspection angles while still retaining the good patient coverage without a patient having to be moved. There is furthermore a good accessibility to the inspection area for a medical staff.

Figure 6:
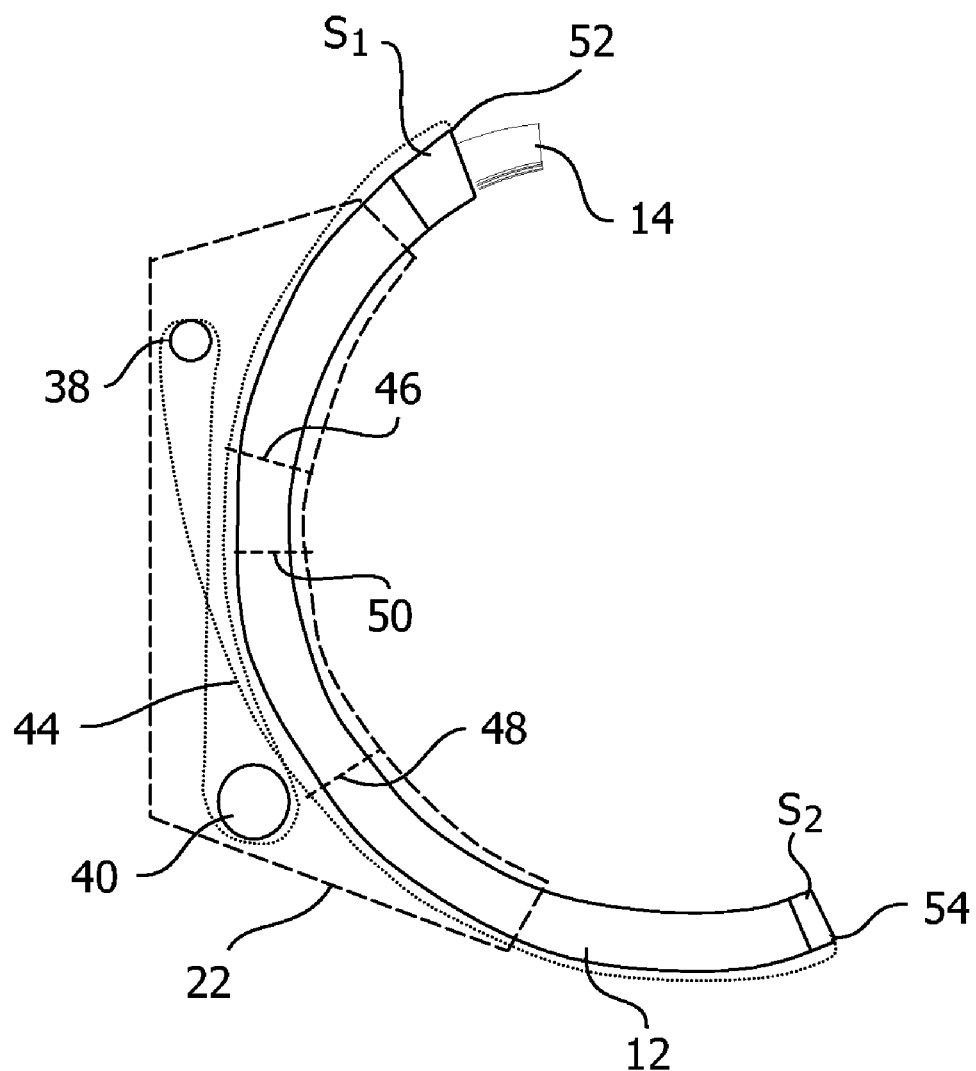

FIG. 6 shows a side view of the relevant parts of an X-ray examining apparatus according to a second embodiment of the present invention using a so-called Z-drive structure for rotating the main arm. There are some differences here in relation to the first embodiment. Here there is only the first auxiliary arm 14 present. The second auxiliary arm is not necessary and the X-ray source is connected directly to the main arm 12 instead (not shown) but in the same way as in the first embodiment, via a tap defining a second pivot point. The first auxiliary arm is able to move out from a first end section S1 of the main arm. The holder 22, which is indicated by a structure outlined with dashed lines, does furthermore have a special configuration. Also here there is provided a first guiding system, which may be in the form of a track as in the first embodiment. The first auxiliary arm 14 can be provided with a bar and a fastener providing a first pivot point in the same way as in the first embodiment (not shown). The main arm 12 is here connected to a timing belt 44 at a first 52 and a second 54 connection point, where the first connection point 52 is provided at a first end section S1 of the main arm 12, from which the first auxiliary arm 14 projects and the second connection point 54 is provided at a second opposite end section S2 of the main arm 12 (where the X-ray source is provided). The belt 44 is here indicated by a dotted line. The holder 22 is furthermore provided with a first guiding pulley 38 and a second guiding pulley 40. The belt 44 here runs from the first connection point 52 along the first timing pulley 38, over the second timing pulley 40, over the first timing pulley 38 and along the second timing pulley 40 to the second connection point 54, in this order, at any rate, wherein, in a central position 50 of the main arm, the first timing pulley 38 is positioned in closer proximity of the first connection point 52 than of the second connection point 54 and the second timing pulley 40 is positioned in closer proximity of the second connection point 54 than of the first connection point 52. By having the belt 44 run over the first and second timing pulleys 38 and 40 a zigzag configuration of the belt 44 is created. This enables the connection points 52 and 54 to come past the first and the second timing pulleys 38 and 40 respectively when the main arm 12 is rotated so that a large angular range is obtained.

With this configuration it is possible to rotate the first end section S1 having the first connection point 52 past the central position 50 all the way to a first extreme position 48 (indicated by a dashed line) below the second timing pulley 40 as well as to rotate the second end having the second connection point 54 past the central position 50 to a second extreme position 46 (indicated by a dashed line), which may be provided above the first timing pulley 38. In this way a wide range of projection angles are provided. As can be seen this second embodiment allows the main arm to be moved further than in the first embodiment, why it is not necessary to have the second auxiliary arm for obtaining a wider range of projection angles.

By the use of the first auxiliary arm which here has a shape that corresponds to the shape of the end section, it is furthermore possible to move this first auxiliary arm 14 out from the first end section S1 and around the isocentre, in the same way as in the first embodiment. This allows the provision of a wider patient coverage. The X-ray source and the X-ray detector can here furthermore also be turned round first and second pivot points in the same way as in the first embodiment in order to align the X-ray source with the X-ray detector (not shown). This can here be combined with some movement of the main arm so that the second end section S2 is brought further away from the central position 50. In this way this second embodiment also provides a wide range of projection angles together with a good patient coverage.

There are a number of further variations that are possible to make in relation to the present invention. The bar need not to be provided at the first auxiliary arm, but can just as well be provided at the other arm, i.e. the second auxiliary arm or the main arm depending on the embodiment. In fact the bar is not necessary for the functioning of the apparatus, but can be excluded from the apparatus. In this case an X-ray detector may be connected directly to the corresponding arm via a tap. The X-ray source can furthermore be provided on the second auxiliary arm or the main arm and the X-ray detector on the first auxiliary arm. The main arm need not be shaped as a C. It can have any shape allowing turning of the main arm around the isocentre. It can for instance be shaped as a G-arc or as a part of an ellipse. There can furthermore be several extension segments provided between an end section of the main arm and a corresponding auxiliary arm, where the extension segments and the auxiliary arm can be telescopically moved out of the main arm.

In the first embodiment the length of the auxiliary arms can be varied in dependence of how wide inspection angles that are desired. The first and second auxiliary arms need not have to have the same lengths, for instance if different inspection angles are needed for clockwise and counterclockwise movements. The only limitation is that they cannot together be longer than the main arm. The first and second auxiliary arms need not be adapted in shape to the whole of the main arm. It is sufficient that they are adapted in shape to the end sections.

In the second embodiment the first auxiliary arm need not have the shape described. It can for instance be straight or have some other rotational point as long as it always stays within the system volume defined by the curvature of the main arm. It is also possible for the first auxiliary arm to also move inwards into the main arm, like in the first embodiment. It should also be realized that the second embodiment may use two auxiliary arms in the same way as in the first embodiment.

Although the present invention has been described in connection with specific embodiments, it is not intended to be limited to the specific form set forth herein. Rather, the scope of the present invention is limited only by the accompanying claims. In the claims, the term comprising does not exclude the presence of other elements. Additionally although individual features may be included in different claims, these may possibly be advantageously combined and the inclusion in different claims does not imply that a combination of features is not feasible and/or advantageous. In addition singular references do not exclude a plurality. Thus references to "a", "an", "first", "second" etc. do not preclude a plurality. Reference signs in the claims are provided merely as a clarifying example and shall not be construed as limiting the scope of the claims in any way.

The invention claimed is:

1. An x-ray examination apparatus comprising:
   first and second radiation modules in the form of an x-ray source and an x-ray detector;
   a main curved arm having first and second end sections;
   a first auxiliary arm provided at the first end section of the main curved arm;
   the first auxiliary arm carrying the first radiation module on a bar pivotably attached to the first auxiliary arm;
   the second radiation module being pivotably coupled to the second end section of the main curved arm;
   the first auxiliary arm having a shape that complements the curvature of said main curved arm at least at said first end section and being movable with respect to this end section of the main curved arm at least in a direction away from it.

2. An x-ray examination apparatus according to claim 1, wherein the first auxiliary arm is being movable with respect to its end section of the main curved arm in a direction inwards along the first end section.

3. An x-ray examination apparatus according to claim 1, further comprising a second auxiliary arm provided at the second end section of said main curved arm, the second auxiliary arm pivotably carrying the second radiation module, being movable with respect to its second end section of the main curved arm at least in a direction away from said second end section and having a shape that complements the curvature of said main curved arm at least at said second end section.

4. An x-ray examination apparatus according to claim 3, wherein the second auxiliary arm is being movable with respect to its second end section of the main curved arm in a direction inwards along the second end section.

5. An x-ray examination apparatus according to claim 3, wherein the combined lengths of said first and second auxiliary arms are equal to or less than the length of the main curved arm.

6. An x-ray examination apparatus according to claim 1, wherein each radiation module is connected to a corresponding arm using a mechanical coupler, each coupler allowing the turning of a radiation module round an axis of rotation provided through the corresponding mechanical coupler that is transverse to the movement of the corresponding arm.

7. An x-ray examination apparatus according to claim 6, wherein one mechanical coupler provided for one radiation module is connected to a bar stretching inwards in a direction towards the other radiation module allowing movement of said one radiation module along said bar.

8. An x-ray examination apparatus according to claim 1, further comprising a holder for moving the main curved arm using a curved first guiding system, where the curvature of said first curved guiding system for the main curved arm defines an isocentre around which the main curved arm is turned and the main curved arm includes at least one second guiding system allowing movement of said first auxiliary arm around said isocentre.

9. An x-ray examination apparatus according to claim 8, wherein the main curved arm is rotatable with respect to the holder via a central position between first and second extreme positions, said holder comprising first and second timing pulleys and a belt which is attached to the main curved arm via first and second connection points, wherein at any rate in a central position of the main arm, the belt runs from the first connection point in a zigzag configuration over the first and second timing pulleys to the second connection point.

10. An x-ray examination apparatus according to claim 9, wherein at the central position of the main curved arm the zigzag configuration of the belt is present because the belt runs from the first connection point, along the main curved arm, around the second timing pulley, around the first timing pulley, and along the main curved arm to the second connection point, allowing the first and second connection points to come past the first and second timing pulleys, respectively.

11. An x-ray examination apparatus according to claim 9, wherein said second radiation module is connected to the main arm.

12. An x-ray examination apparatus according to claim 1, further comprising a motion control unit arranged to control the movements of all movable elements of the apparatus to make the radiation modules always face each other.

13. A method for obtaining an x-ray examination comprising providing an apparatus according to claim 1, placing a patient to be examined within the system volume, adjusting the positions of the source and detector, and detecting x-rays from the source.

14. A method for performing a medical inspection comprising providing an apparatus according to claim 1, placing a patient to be examined within the system volume, adjusting the positions of the source and detector, and detecting x-rays from the source.

* * * * *